(12) United States Patent
Dellaca' et al.

(10) Patent No.: US 7,325,545 B2
(45) Date of Patent: Feb. 5, 2008

(54) SYSTEM AND METHOD FOR THE AUTOMATIC DETECTION OF THE EXPIRATORY FLOW LIMITATION

(75) Inventors: Raffaele Dellaca', Como (IT); Andrea Aliverti, Como (IT); Antonio Pedotti, Milan (IT)

(73) Assignee: Politecnico di Milano, Milan (IT)

( * ) Notice: Subject to any disclaimer, the term of this patent is extended or adjusted under 35 U.S.C. 154(b) by 49 days.

(21) Appl. No.: 11/002,368

(22) Filed: Dec. 2, 2004

(65) Prior Publication Data

US 2005/0178385 A1     Aug. 18, 2005

Related U.S. Application Data

(63) Continuation of application No. PCT/EP03/06119, filed on Jun. 10, 2003.

(30) Foreign Application Priority Data

Jun. 11, 2002    (IT)    .................. MI2002 A 001273

(51) Int. Cl.
    *A61M 16/00*      (2006.01)
    *A61M 15/00*      (2006.01)
    *A61B 19/00*      (2006.01)
    *A61B 5/08*       (2006.01)

(52) U.S. Cl. .................... 128/204.23; 128/200.24; 128/204.18; 128/898; 600/533; 600/532

(58) Field of Classification Search ............... 600/533, 600/532; 128/204.18, 204.21, 204.23, 200.24, 128/200.26, 897, 898

See application file for complete search history.

(56) References Cited

U.S. PATENT DOCUMENTS 3,621,833 A * 11/1971 Crane ..................... 600/533

4,122,839 A * 10/1978 Franetzki et al. .......... 600/533
4,197,859 A     4/1980 Prestele (Continued)

FOREIGN PATENT DOCUMENTS

EP            0373585       6/1990

OTHER PUBLICATIONS

M. Vassiliou; R. Peslin; C. Saunier, C. Duvivier; "Expiratory Flow Limitation During Mechanical Ventilation Detected by the Forced Oscillation Method," European Respiratory Journal, pp. 779-786, 1996.

(Continued)

*Primary Examiner*—Justine R. Yu
*Assistant Examiner*—Annette Dixon
(74) *Attorney, Agent, or Firm*—King & Schickli, PLLC

(57) ABSTRACT

The present invention refers to a system and a method for the automatic detection of the expiratory flow limitation of a subject. In an embodiment thereof the system for the automatic detection of expiratory flow limitation of a subject comprises determining the respiratory impedance of the subject comprising an imaginary component and, eventually, of a real part or, at least, by applying a forcing signal with one or more spectral components to the airway opening of a subject combined with measuring time courses of pressure and flow at the airway opening; determining at least one index linked to respiratory impedance or pressure and flow time courses; indicating the positioning of at least one index in relation to a preset threshold value.

16 Claims, 6 Drawing Sheets

U.S. PATENT DOCUMENTS

| | | | |
|---|---|---|---|
| 4,259,967 A * | 4/1981 | Vooren et al. | 600/533 |
| 4,326,416 A * | 4/1982 | Fredberg | 600/533 |
| 5,318,038 A * | 6/1994 | Jackson et al. | 600/533 |
| 5,513,648 A * | 5/1996 | Jackson | 600/529 |
| 6,066,101 A | 5/2000 | Johnson et al. | |
| 6,079,412 A * | 6/2000 | Meier et al. | 128/204.23 |
| 6,142,952 A * | 11/2000 | Behbehani et al. | 600/533 |
| 6,257,234 B1 * | 7/2001 | Sun | 128/204.18 |
| 6,377,845 B1 * | 4/2002 | Kinast | 600/547 |
| 6,415,791 B1 * | 7/2002 | Van Brunt | 128/204.18 |
| 6,435,182 B1 * | 8/2002 | Lutchen et al. | 128/204.21 |
| 6,473,640 B1 * | 10/2002 | Erlebacher | 600/547 |
| 2001/0039950 A1 * | 11/2001 | Scholler et al. | 128/204.18 |

OTHER PUBLICATIONS

A.-M. Lauzon; J. H. T. Bates; "Estimation of Time-Varying Respiratory Mechanical Parameters by Recursive Least Squares," J. Appl. Physiol 71, pp. 1159-1165, 1991.

* cited by examiner

SYSTEM AND METHOD FOR THE AUTOMATIC DETECTION OF THE EXPIRATORY FLOW LIMITATION This application is a continuation of international PCT application number PCT/EP03/06119 (published in English on Dec. 18, 2003 as WO 03/103493 A1) filed Jun. 10, 2003, entitled SYSTEM AND METHOD FOR THE AUTOMATIC DETECTION OF THE EXPIRATORY FLOW LIMITATION, claiming priority to Italian Application No. MI2002 A 001273 filed Jun. 11, 2002. The contents of these applications are expressly incorporated herein by reference.

1. Field of the Invention

The present invention refers to a system and a method for the automatic detection of the expiratory flow limitation in patients.

2. Background of the Invention

The human respiratory system is characterised by the phenomenon called expiratory flow limitation, that is by the fact that during expiration the flow of gases expelled depends on the expiratory pressures only up to a certain threshold value, beyond which the flow cannot be increased even if expiratory pressures are increased. The threshold value is function of the lung volume (being higher at high volumes then decreasing with the reduction of the lung volume) and is, in healthy subjects, considerably higher than the maximum flows obtained during spontaneous breathing. The difference between maximum expiratory flow and expiratory flow during spontaneous breathing measured at the same lung volume constitutes the reserve of expiratory flow. Such reserve is used in situations such as physical exercise, in which the metabolic requirements and, consequently, the lung ventilation increase. The resulting increase of the tidal volume and of the respiratory frequency therefore requires the increase of both inspiratory and expiratory flows. Several obstructive pathologies of the respiratory system (chronic obstructive pulmonary disease or COPD, asthma, . . . ) modify the mechanical properties of airways and lung parenchyma, notably reducing the reserve values of expiratory flow until it is annulled. In addition, the reduction can be so marked that it forces the patient to breathe at higher lung volumes than usual to make use of the dependence of the maximal flow on lung volume and to obtain the expiratory flows needed for a correct gas exchange. This phenomenon is knows as "dynamic hyperinflation". Breathing at higher lung volumes, however, means both using the inspiratory muscles in a geometric condition which is unfavourable to them (reduced muscular length and consequent reduction of the capacity to produce force) and having the thoracic wall expanding to volumes at which it is more stiff. All these effects combine to determine a significant increase in the respiratory work, excessively tiring the respiratory muscles and thus limiting the capacity of the patient to carry out even simple physical activity. To know whether a patient is flow-limited during spontaneous breathing is therefore of fundamental importance for the diagnosis and definition of the rehabilitation and pharmacological therapy, as well as the assessment of their effectiveness.

As of today the methods used for identifying whether a subject is limited in the expiratory flow can be divided into two main categories: those based on the measurement of the oesophageal pressure and those that do not use this measurement. The former are currently considered the only reliable ones, but they require a latex balloon connected to a catheter-pressure transducer system for measuring the oesophageal pressure to be inserted into the lower third of the oesophagus. Esophageal pressure is considered an excellent estimate of the pleural pressure and therefore it allows the estimation of alveolar pressure. From the relationship between alveolar pressure and flow at the airway opening it is possible to assess the presence of expiratory flow limitation during quiet breathing in different ways (for example studying the so called "isovolume pressure flow curves" or analysing Mead and Whittenberger graphs). Unfortunately this procedure is invasive and it is not tolerated by a large percentage of subjects, in addition it requires a lot of time (both for the insertion of the balloon and for the patient to adapt to it) and it may significantly alter the breathing pattern of the subject.

The methods belonging to the second category are based on the determination of the flow-volume curves carried out in body plethysmograph and on the application of negative pressure to the airways during the expiratory phase or on abdominal compression. However these methods are characterised by both theoretical and practical limitations and therefore they are usually considered not very reliable and, in the first case, require the collaboration of the subject.

A study by M Vassiliou, R. Peslin, C. Saunier, C. Duvivier, entitled "Expiratory flow limitation during mechanical ventilation detected by the forced oscillation method", European respiratory Journal, 1996, suggests a method for determining expiratory flow limitations based on the forced oscillations technique able of indicating the possible presence of expiratory flow limitation induced by bronco constrictor drugs (methacholine) in rabbits submitted to mechanical ventilation. In this study it can be observed that expiratory flow limitation is responsible for systematic variations of the imaginary part (Xrs) of the total respiratory input impedance (Zrs) in mechanical models of a single collapsible airway and in mechanically ventilated rabbits. It is believed that the analyses described in the article mentioned above were carried out under extremely critical and particular conditions, that is on mechanically ventilated animals in which the limitation of the expiratory flow was induced pharmacologically and on mechanical models that simulate the behaviour of oniy one single airway and that therefore they do not reproduce real conditions occurring in humans with obstructive diseases (hundreds of thousands of airways placed in series and in parallel in the tracheal-bronchial tree constricted in a very heterogeneous pattern).

SUMMARY OF THE INVENTION

In view of the state of the technique, the object of the present invention is to provide a method and a system for assessing automatically in a non-invasive manner whether the expiratory flow limitation is present or not in a subject, without requiring subject collaboration and continuously in time.

In accordance with the present invention, said object is achieved by means of a system for the automatic detection of expiratory flow limitation of a subject comprising: means for determining the respiratory impedance of said subject composed of a real component and an imaginary component; means for determining at least one index linked to said respiratory impedance; means for indicating the positioning of said at least one index in relation to a preset threshold value.

In accordance with the present invention, said object is also achieved by means of a Method for the automatic detection of the expiratory flow limitation of a subject comprising the phases of: determining the respiratory impedance of said subject composed of a real component and an imaginary component; determining at least one index linked to said respiratory impedance; indicating the positioning of said at least one index in relation to a preset threshold value.

Thanks to the present invention it is possible to study patients in an absolutely non-invasive manner, without requiring their collaboration, under very different conditions, (during spontaneous breathing at rest, exercise, mechanical ventilation and various respiratory manoeuvres such as vital forced and slow capacities, maximum voluntary ventilation, etc.). In addition, it allows to study subjects in various postures (erect, sitting, supine, prone).

In addition, it permits automatically, without any intervention, to detect the presence of expiratory flow limitations.

BRIEF DESCRIPTION OF THE DRAWINGS

The characteristics and advantages of the present invention will appear evident from the following detailed description of an embodiment thereof, illustrated as non-limiting example in the enclosed drawings, in which.

DETAILED DESCRIPTION OF THE INVENTION FIGURES

Figure 1:
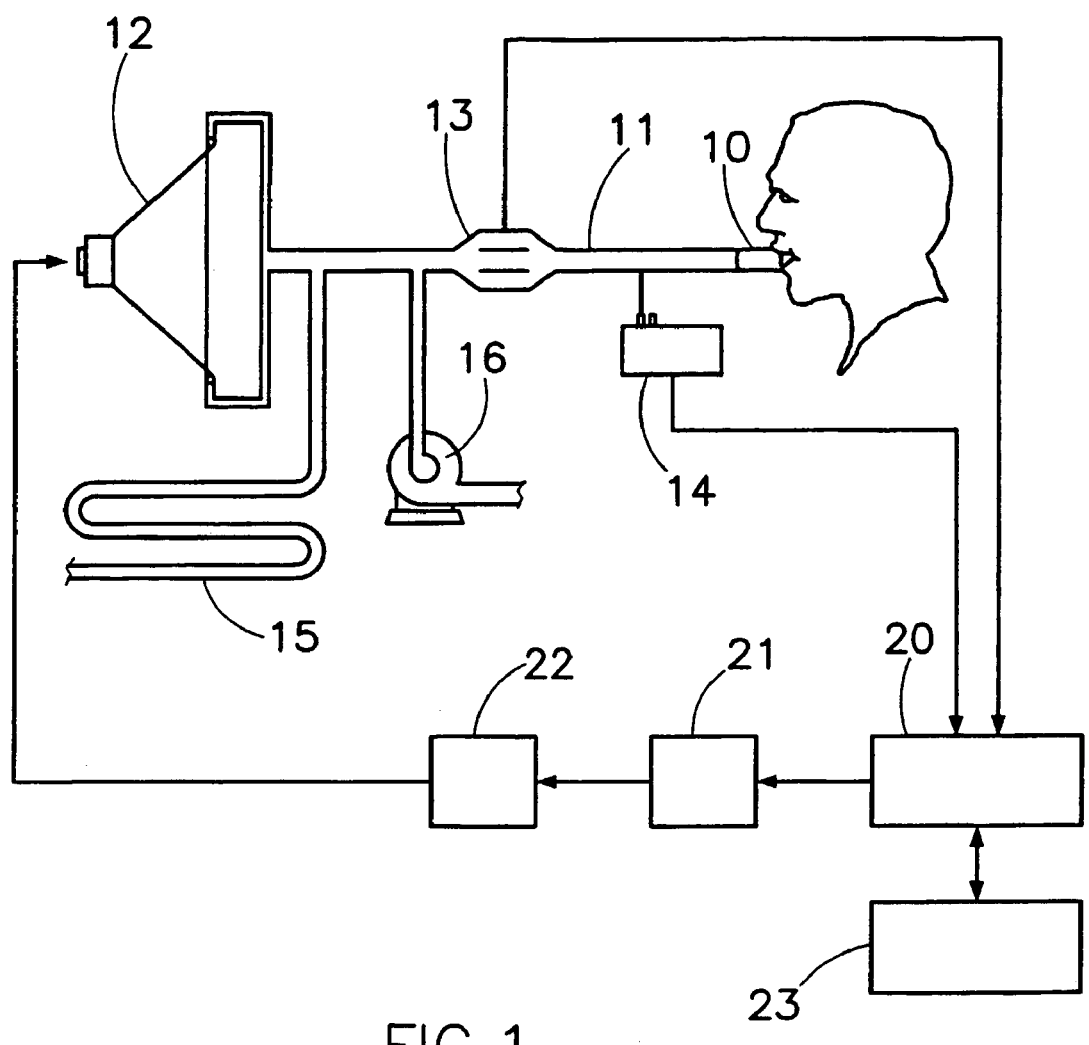
FIG. 1 shows schematically a system for the automatic detection of the expiratory flow limitation of a patient in accordance with the present invention.

In FIG. 1 the airways of a patient are connected by means of a mouthpiece 10 to a duct 11 that is connected to a loudspeaker 12. A sensor device 13 for measuring the flow of air inside and a sensor device 14 for measuring the air pressure is applied to the duct 11. A tube 15 at high inertia and an aspirator 16 are also applied to the duct.

The electrical signals related to the measurements of flow and pressure, supplied respectively by the devices 13 and 14, are connected to the circuits 20 of analogical-digital (A/D) and digital-analogical (D/A) conversion. The circuits 20, controlled by a microprocessor of computer 23, provide an output signal that is applied in succession to a low pass filter 21, to a power amplifier 22 and then to a loudspeaker 12.

The determination of the time course of the respiratory impedance during the spontaneous breathing is carried out by applying a pressure signal to the airway opening of the patient consisting of the summation of one or more sinusoids among which at least one has a frequency no higher than 15 Hz. For example 4 sinusoids at frequencies of 2.5 Hz, 5.5 Hz, 9.5 Hz and 17.5 Hz.

Said pressure signal must preferably have an amplitude between 1-4 $cmH_2O$ peak-peak (with the pressure generator connected to a resistive load of 2 $cmH_2O/L*s$); in any case the amplitude of the stimulus signal should not exceed 5 $cmH_2O$ to avoid distortions due to the non-linearity of the respiratory system. The pressure signal, generated in the example in FIG. 1 by a loudspeaker, can be generated by cylinder-piston systems or by suitable servo-controlled valves. For simplicity in the rest of the description we shall refer to the pressure generator consisting of a loudspeaker, even though this choice is not bound to the functioning of the method herein presented as other devices can be used for this purpose (piston pumps, servo-controlled valves, etc.). The pressure waves generated are applied to the airway opening of of the subject by means of a duct 11 in which the flow measuring devices 13 and pressure measuring devices 14 are housed. By airways opening we intend mouth, nose, tracheostomy, etc. Thus pressure and flow are measured, preferably near the entrance of the airways (if a long connection tube is used between the flow and pressure sensors and the subject the measurements must be corrected for mechanical properties of the tube). To enable the subject to breathe spontaneously during the measurement, a tube 15 connects the output of the generator of pressure waves with the outside environment. This tube is sized and shaped so as to offer a high impedance to high frequencies generated by the loud-speaker, while at the low frequencies of the spontaneous breathing the impedance must result very low (better if less than 1-2 $cmH2O/L/*s$ for signals of frequency lower than 5 Hz). The large dimensions of this tube (length about 1 m and diameter about 3-4 cm) introduce considerable dead space, such as not to allow the subject to breathe ambient air. To reduce this dead space, an aspirator 16 (or a compressor) can be used which is able of producing a flow of about 0.2-0.4 l/s (independent from the oscillating pressure) that permits the expulsion of the gases expired by the subject and, thus, the exchange of the air contained in the tube. In alternative to the long tube 15 other systems with a similar function can be used, including a simple resistance of 2-3 $cmH_2O/L*s$ connected between the generator and the flow measuring device to the atmosphere.

The flow and pressure signals are digitised at a proper sampling frequency, paying attention to avoid aliasing phenomenon by means of appropriate filters.

From the analysis of the variations of Ms during a single respiration, it has been observed that during spontaneous breathing the flow-limited patients presented considerable reductions in the reactance values measured in the expiratory phase. In addition, similar reductions were also discovered in healthy subjects during maximum forced expirations and, thus, in flow-limitation condition. The explanation of such phenomenon should be as follows. During the expiratory flow-limitation there are points of the airways distributed in the tracheo-bronchial tree (called choke points) in which the speed of propagation of the pressure wave becomes equal to that of the expired air. In these conditions eventual variations of pressure applied to the two ends of the tree (alveoli and airways opening) cannot exceed the choke points, and thus the flow no longer results to be dependent on the difference of pressure applied. The pressure oscillations applied at the opening of the airways with the above-described techniques cannot thus reach the alveoli during the expiratory flow limitation condition.

The inertance of the respiratory system at the frequencies considered is basically due to the upper airways and, at low frequencies, it assumes a marginal role in the definition of Xrs.

The compliance of the respiratory system is mainly due to the alveoli, as the compliance of the walls of the airways, additive to the former, results in being far lower, as is also that due to the quantity of air contained in the bronchial tree. The apparent 'closing' of the airways at the choke points thus causes the exclusion of the alveolar compliance from the measurement, producing a substantial reduction of the compliance observed, which in this condition is prevalently due to the airways walls. A reduction of the apparent compliance causes an increase of the negative component of Xrs and, thus, a substantial reduction of it during the expiratory phase if in the presence of flow-limitation.

Various methods can be used to calculate the input impedances of the respiratory system. That used in accordance with the present invention must be capable of calculating the time courses of the impedance during spontaneous breathing at a frequency of at least 5-10 Hz. The various methods for separating the components of the signal due to spontaneous breathing from those due to the forcing can in particular be based on the cross-correlation, the FFT or the estimation by least squares. These operations are carried out by the computer 23. In accordance with the present invention a method based on least square is used.

To be able to apply this method the stimulus signal S.sub.stim must be a sinusoid or a sum of N sinusoids of known periods T1, T2, . . . TN 1 S stim (t)=K i=1 N sin(2 T it+i)

$$S_{stim}(t) = K \sum_{i=1}^{N} \sin\left(\frac{2\pi}{T_i} t + \varphi_i\right)$$

with the following conditions:

$\forall i\ T_i \ll T_{resp}$ e $T_i \gg T_c$ where Tresp is the respiratory period and Tc is the sampling period.

The calculation proceeds in an iterative manner: each iteration processes a number of pressure samples equal to W and a number of flow samples equal to W. At the k-th iteration the samples from the k-th to the (k+W−1)-th are processed, the result is assigned to the time k+W/2 if W is even, and to the time k+(W−1)/2 should W be odd; the following is carried out under the hypothesis that W is even. The choice of parameter W is not critical, as W samples do not have to contain exactly a period of the stimulus signal. As we shall see further ahead in fact, the theory imposes W≧1+2N, by increasing said parameter minor influence of the noise is obtained but at the same time the faster variations of impedance are lost and the calculation times are lengthened. A good compromise between sensitivity to the noise and to the variations of impedance can be obtained using for W the minimum number of samples that a whole period of the slowest stimulus component contains.

Each iteration is composed of 2 steps.

First of all there is the extraction of the pressure and flow signals of the components due to the respiration and calculation of the coefficients to describe the components due to the stimulus in phasor notation.

For each signal a linear combination of N frequency sinusoids of frequencies equal to the stimulus frequencies is associated:

$$S(t) = r(t) + a_0 + \sum_{i=1}^{N} a_i \cos(2\pi f_i t) - b_i \sin(2\pi f_i t) =$$

$$r(t) + a_0 + \sum_{i=1}^{N} Re[(a_i + jb_i)e^{j2\pi f_i t}]$$

where r(t) represents the noise and Re the real part of a complex number.

As the signals are at discrete time, we have for the pressure:

$S_P = A \cdot X_P + R_P$ with:

$$A = \begin{bmatrix} 1 & \cos(\omega_1 t_1) & -\sin(\omega_1 t_1) & \dots & \cos(\omega_N t_1) & -\sin(\omega_N t_1) \\ 1 & \cos(\omega_1 t_2) & -\sin(\omega_1 t_2) & \dots & \cos(\omega_N t_2) & -\sin(\omega_N t_2) \\ \dots & \dots & \dots & \dots & \dots & \dots \\ 1 & \cos(\omega_1 t_W) & -\sin(\omega_1 t_W) & \dots & \cos(\omega_N t_W) & -\sin(\omega_N t_W) \end{bmatrix}$$

$$S_P = \begin{bmatrix} P(k) \\ P(k+1) \\ \dots \\ P(k+W-1) \end{bmatrix} \quad X_P = \begin{bmatrix} a_{P,0}(k+W/2) \\ a_{P,1}(k+W/2) \\ b_{P,1}(k+W/2) \\ \dots \\ a_{P,N}(k+W/2) \\ b_{P,N}(k+W/2) \end{bmatrix} \quad R_P = \begin{bmatrix} r_P(k) \\ r_P(k+1) \\ \dots \\ r_P(k+W-1) \end{bmatrix}$$

where $\omega_i = 2\pi/T_i$ pulsation of the i-nth component of the stimulus, $t_j = (j-1)TC$ time associated to the j-th sample of the W selected.

Note that the matrix A remains identical for all the iterations.

Such a system allows a solution to the least square as long as W≧1+2N, and the solution to the least square is given by:

$X_P = (A^T A)^{-1} A^T S_P$

As a remains identical for all the iterations, it is possible to calculate $B = (A^T A)^{-1} A^T$ once and reduce the problem to a vector-matrix product: $X_P = B\, S_P$.

The coefficient $a_0$ represents the component of the signal due to the respiration while the coefficients ai and bi enable the component of the pressure signal due to the stimulus to the i-th frequency to be written in phasor notation.

The same procedure is applied to the flow signal.

Thus the impedance is calculated at the various stimulus frequencies and at the time k+W/2 as ratio between the signal phasors:

$$z_i(l) = \frac{a_{P,i}(l) + jb_{P,i}(l)}{a_{v,i}(l) + jb_{v,i}(l)}$$

where l=k+W/2 and 1<i<N and Zi is the impedance to the i-nth stimulus frequency.

Each iteration requires 2(W−1)(1+2N) sums and 2W(1+2N) products between real numbers, and N ratios between complex numbers; therefore this method can be competitive in comparison to other methods in terms of execution speed. This calculation method thus enables us to obtain the time progresses of the impedance at numerous frequencies, with the possibility of freely choosing these frequencies, as long as the second requisite is respected. It is important to point out that this method provides time progresses of the impedance filtered with a moving average filter of amplitude W.

The possibility of varying the parameter W permits the choice of the most suitable compromise between sensitivity to the noise and passing band of that filter.

To be able to reduce the impact of the noise on the assessment of the impedance in the case of multifrequency signals with a high number of components (N>3-4) the method proposed above can be modified as follows.

The pressure and flow signals are decomposed in a component due to the respiration and N components due to the various frequencies of the stimulus by means of a series of numeric Butterworth filters of suitable order (typically of the 4th order). A low-pass filter with cut-off frequency of suitable frequency (1-3 Hz for spontaneous breathing) separates the component due to the respiration, a series of N band-pass filters instead separates the components due to the various stimulus sinusoids. The i-nth band-pass filter has a passing band centred on the i-th frequency of the stimulus signal and an adjustable bandwidth $BW_i$. Using this procedure N couples of pressure and flow signals are obtained from the couple of pressure and flow signals in input, each relating to a certain component of the stimulus. Then we proceed to the calculation of the N impedances relating to the N stimulus frequencies using the method proposed above.

The method proposed first is thus used in monofrequency modality in this variant, given that the couple of signals that is passed contain only one dominating frequency.

The effect of the decomposition of the signals with the band-pass filters is to obtain couples of signals with a better signal/noise ratio than that of the starting couple of signals. In fact, as the respiratory system is not linear, the spectrum of the original pressure and flow signals will also contain, in addition to the stimulus frequencies and to the background noise, all the harmonics of such frequencies and the spurious frequencies generated by the crosstalk effect. If N stimulus frequencies are chosen according to a pattern that excludes the possibility that a frequency is a whole multiple of any other component of the signal, it is possible to prevent the harmonics from falling on the N frequencies chosen; opting instead for a pattern of the type non-sum non-difference of order 2 or greater, the spurious frequencies generated by the crosstalk are prevented from falling on the N frequencies of the stimulus. In this manner, the effect of a narrow band-pass centred on the i-nth frequency of stimulus will be to remove the background noise, the other N−1 components caused by the stimulus, all the harmonics and also the spurious frequencies, thus improving the signal/noise ratio.

The parameter BWi must be sized taking into account several considerations. The variation in the time of the impedance at the frequency i-th Zi(t) is reflected in an amplitude modulation of the pressure and flow signals, this means that the spectrum of said signals will contain, besides the frequencies of the stimulus with their harmonics and the background noise, also the components around the stimulus frequencies due to the amplitude modulation of the signals. For the theory of the signals, this surrounding has semiamplitude equal to the maximum modulation frequency, a frequency that here corresponds to the fastest of the spectrum components of the impedance. The parameter BWi sets the width of the surrounding considered for the i-th frequency, then limits the speed of variation that can be observed of Zi(t) at BWi/2 Hz. Therefore, also the choice of the parameter BWi constitutes a compromise: keeping the value of BWi low the background noise and the harmonics of the stimulus are eliminated more effectively, but at the same time the fastest variations of Zi(t) are lost; vice versa, a high value of BWi permits even the fastest variations of Zi(t) to be gathered but does not effectively remove the background noise and the harmonics of the stimulus signal.

Finally it can be noted that the parameters BWi and Wi both have the collateral effect of limiting the maximum speed of variation that can be observed in Zi(t), with the band-pass filter that is applied before the filtering by mobile media actuated by the method. Consequently, it is advisable that the limitation in frequency on Zi(t) comes about by means of the band-pass. This is achieved by choosing BWi and Wi so that the following relation is met:

$$BW_i < \frac{2fc}{W_i}$$

where fc is the chosen sampling frequency.

Figure 2A:
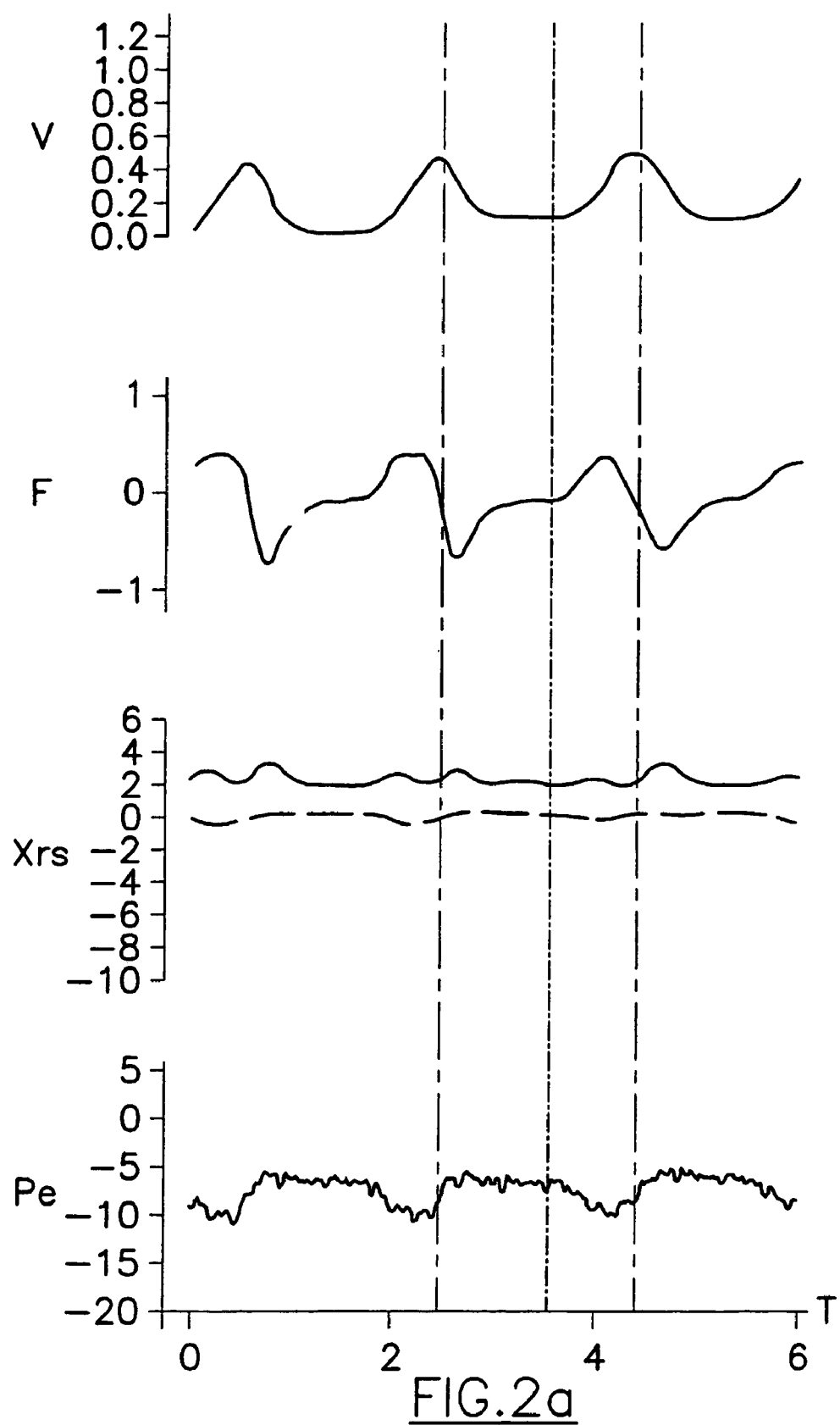
FIGS. 2a, 2b and 2c show the graphics of the volume, the flow, the impedance and the oesophageal pressure of a healthy patient, respectively of a patient with chronic obstructive pulmonary disease (COPD) but not flow-limited and a patient with COPD and flow-limited during spontaneous breathing.
Figure 2B:
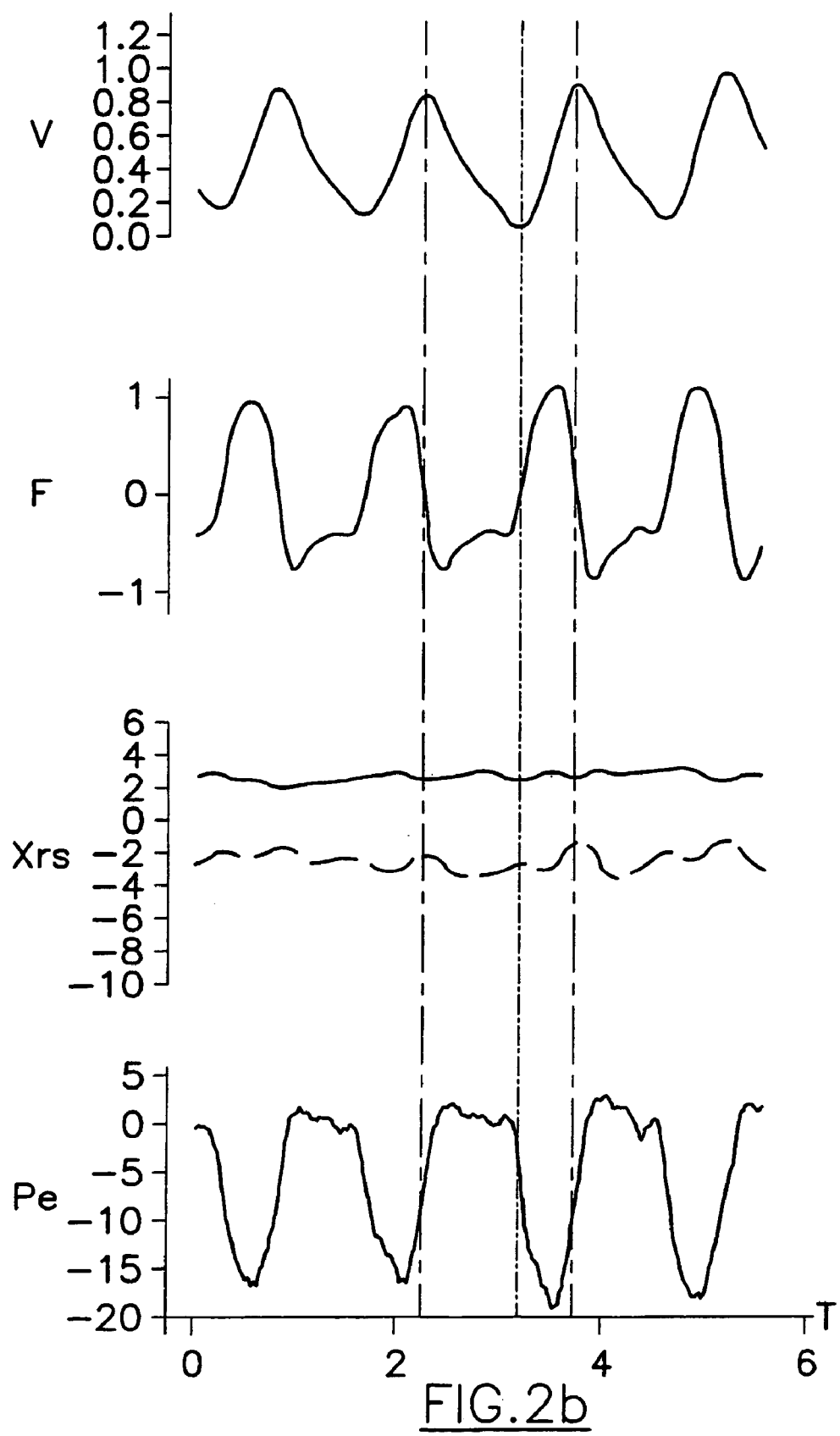
Figure 2C:
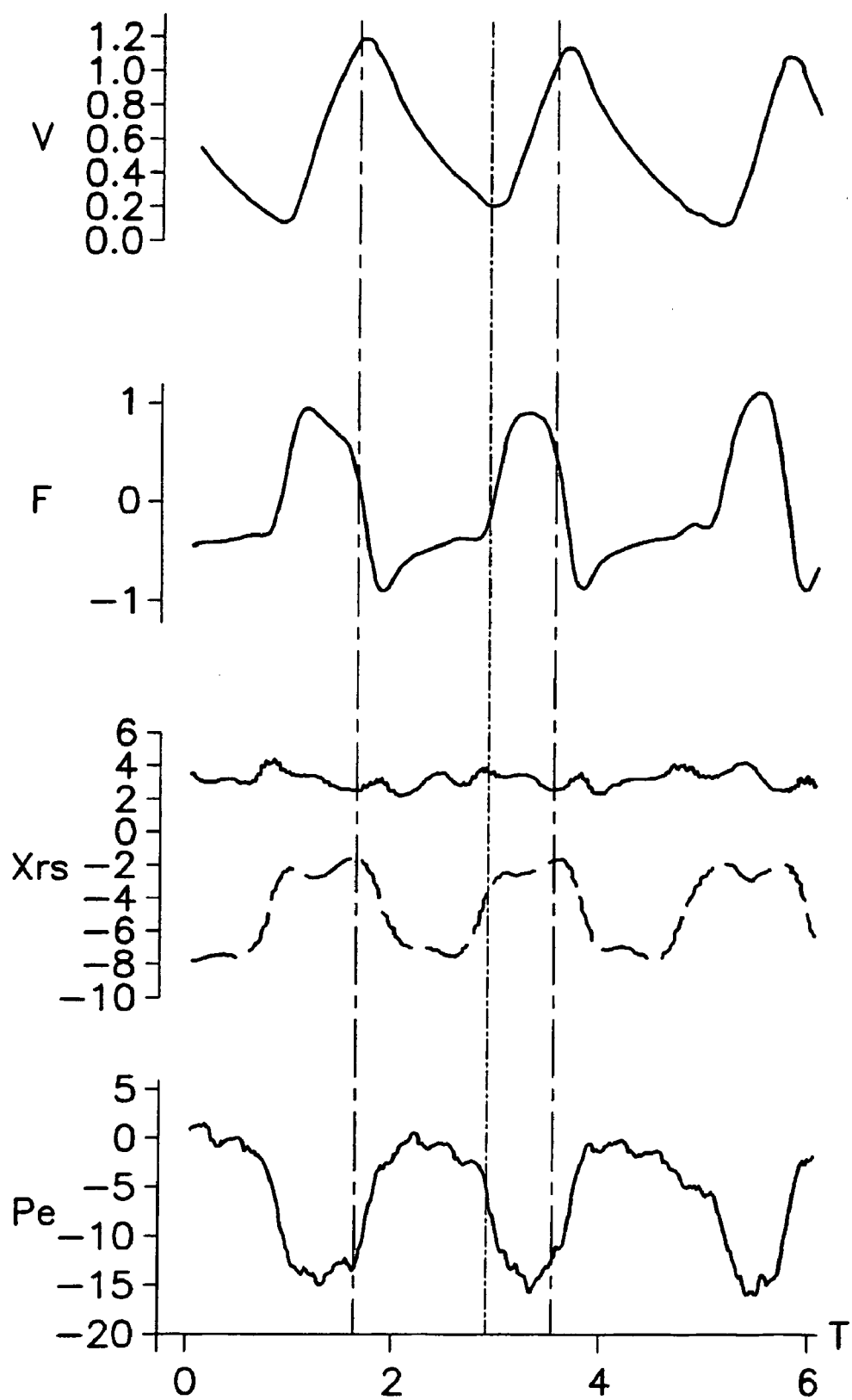

In FIGS. 2a-2c the graphs are shown, upon varying of the time T, the volume V(1), the flow $F(1*sec^{-1})$, the impedance Xrs at 5 Hz (cm $H_2O/1*sec^{-1}$) and the oesophageal pressure Pe (cm $H_2O$) of a healthy patient (FIG. 2a), of a patient with chronic obstructive pulmonary disease (COPD) but not flow-limited (FIG. 2b), and a patient with chronic obstructive pulmonary disease (COPD), with expiratory flow limitation (FIG. 2c).

The graphics of the impedance Xrs show two curves, one in a continuous line for the real part and one with a dotted line for the imaginary part.

In particular take note of the variations of the imaginary part for the patient with chronic obstructive pulmonary disease (COPD), limited flow (FIG. 2c).

The use of the difference between the inspiratory and expiratory values of Xrs can thus be used to identify conditions of expiratory flow limitation calculating the values of suitable indices. In particular some different indices are suggested that can be used both singularly and in combination with each other, said indices are: the minimum value of Xrs reached during the expiration (Xrsm), the average value of Xrs during all or part (for example considering the central third part) of the expiratory phase (Xrsem), the difference between the maximum value of Xrs reached during the inspiratory phase and the minimum value of Xrs reached during the expiration (Xrspp), the difference between the average value of Xrs in all or part of the inspiratory phase and the average value of Xrs during all or part of the expiratory phase (Xrsdm), and the regression coefficient ($r^2$) combined with compliance data obtained fitting the impedance data on a resistance-inertance-compliance series model, the latter only if multifrequency forcing signal is used.

In particular, the latter index is based on the fact that, as already mentioned, during the expiratory flow-limitation (EFL) the measurements of input impedance Zin would reflect only the mechanical properties of the airways between the airway opening and choke points. As already known, it is possible to model expiratory Zin with a simple lumped parameter model consisting of a resistance (R), compliance (C) and inertance (I) in series.

The equation of motion of the respiratory system obtained considering this model is:

$$P = \frac{1}{C}V + R\dot{V} + R\ddot{V} + I\ddot{V}$$

Where P is the pressure at the airway opening and V is the volume measured at the airway opening (eventually obtained integrating the flow), R is the resistance, C the compliance and I the inertance of the whole respiratory system.

This model would be valid for healthy subjects, providing e series of a resistant R, an inductor I and a capacitor C, for the whole respiratory system. The model is invalid for COPD patients without flow limitation due to heterogeneity. However, based on our hypothesis, the model would become valid again for COPD with flow limitation but only during expiration and reflecting only the airways between the mouth and choke points. Now, the R and I represent the resistance and inertance of these airways and the C becomes the airway wall compliance which is the only shunt pathway downstream from the choked airways.

If a multifrequency forcing signal is applied to the subject and the resulting data are used to fit the model, the regression coefficient (r.sup.2) or other indices of the performance of how the model fits the data can be used to discriminate the stabs of subject's airways. In the Table 1 mean.+−.SD of the inspiratory and expiratory values of the parameters estimated on 15 subjects are presented as example. The subjects were aged matched healthy (5 subjects), COPD with no expiratory flow limitation (5 patients) as measured by Mead and Whittenberger method and COPD presenting EFL during quiet breathing (5 patients) accordingly to Mead and Wittenberger method. The C estimated during EFL in COPD were an order of magnitude below the C for healthy subjects, suggesting that in COPD), the C does reflect airway wall compliance rather than parenchymal and chest wall tissues. Moreover, consistenfly with our hypothesis, the simple series model fits COPD patients data well (see r.sup.2 values in Table 1) only during expiration and only if flow limitation is present. This approach then constitutes a potential diagnostic test for identifying the onset of EFL during spontaneous breathing and for estimating the airway wall compliance. The use of the performance index of the model fitting is, in fact, a sensible index of expiratory flow limitation: if it changes to low values to good values passing from expiration to inspiration it means that the subject is flow-limited. Therefore, the time course of the performance index of the model fitting can be used as described for Xrs signal to determine indices and Thresholds for the detection of FFL. Moreover, this approach has potentially the capability of being implemented without passing through the computation of Zin, but fitting directly pressure and flow data to the model (for example as reported in the article of Lauzon, A. M. and J. H. Bates. Estimation of time-varying respiratory mechanical parameters by recursive least squares. J Appl. Physiol 71, 1159-1165, 1991) and computing the performance index time course. This time course can be used similarly to Xrs computing the values of the suggested four indices. For example, to discriminate flow-limited COPD from healthy subjects it is possible to analyse changes of the performance index between inspiration and expiration or to consider also the estimated value for the compliance or both. However, this method based on model fitting, differently from the other indices computed on Xrs only, requires that the forcing signal applied to the subject presents more than two frequency components to have reliable estimations.

TABLE 1

|  |  | EXPIRATION | | | | INSPIRATION | | | |
| --- | --- | --- | --- | --- | --- | --- | --- | --- | --- |
|  |  | R | C | I | $r^2$ | R | C | I | $r^2$ |
| Control | mean | 2.89 | 0.0441 | 0.0075 | 0.85 | 2.58 | 0.0274 | 0.0079 | 0.90 |
|  | SD | 0.10 | 0.0038 | 0.0004 | 0.08 | 0.18 | 0.0042 | 0.0005 | 0.05 |
| COPD NON | mean | 3.56 | 0.0156 | 0.0017 | 0.47 | 3.01 | 0.0144 | 0.0028 | 0.56 |
| EFL | SD | 0.10 | 0.0019 | 0.0006 | 0.09 | 0.02 | 0.0011 | 0.0005 | 0.05 |
| COPD | mean | 3.97 | 0.0032 | 0.0060 | 0.90 | 5.04 | 0.0076 | −0.0025 | 0.36 |
| EFL | SD | 0.08 | 0.0001 | 0.0008 | 0.03 | 0.12 | 0.0006 | 0.0016 | 0.06 |

Figure 3:
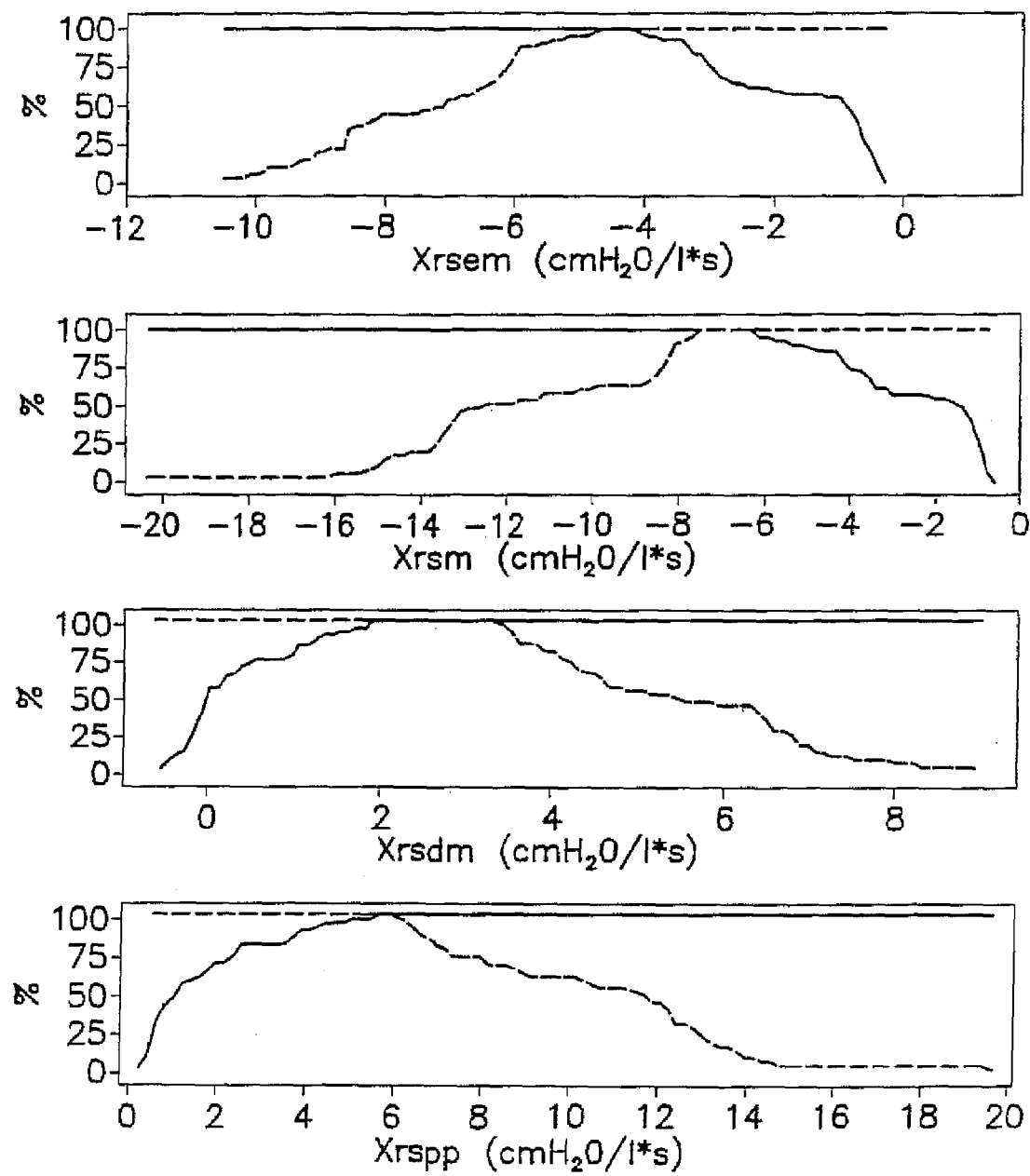
FIG. 3 shows the sensitivity graphics with a continuous line, and specificity with a dotted line, in function of the value adopted as threshold for the various indices in accordance with the present invention.

Once the values of the selected index have been obtained, they are compared with a threshold value, for the mean value during the expiration, that could be equal to 0.77. The exceeding or not of the threshold by the index is used to identify condition of flow-limitation. As an example, the sensitivity values are shown in FIG. 3, with a continuous line, defined as the number of respirations in which the flow-limitation is identified and the number of respirations indicated as flow-limited using the Mead and Whittenberger method (which is a graphic method for detecting the presence of expiratory flow limitation, and it is based on the alveolar pressure vs flow at the mouth graph and it is considered a reliable gold-standard for detecting expiratory flow limitation) and specificity, with a dotted line, defined as the number of respirations in which the absence of flow-limitation is identified and the number of respirations indicated as not flow-limited using the Mead and Whittenberger method as a function of the value adopted as threshold for the various indices analysing a population of COPD patients during spontaneous breathing using a stimulus frequency of 5 Hz. In these graphics it can be seen that the indices based on the reactance guarantee zones in which both sensitivity and specificity are equal to 100%. The use of a threshold value within said zone (for example at its centre) allowed us to define a method for detecting the expiratory flow limitation able to provide equal or better performances than those of the Mead and Whittenberger method but with the important advantage of not requiring the use of the oesophagus balloon. Table 2 shows as an example the optimal values obtained to be used as threshold. Optimal reference values can be obtained also considering equations that take into account other parameters such as, the characteristics of the subjects. As it is possible that subjects who are very different from each other (for example a child and an elderly person) give absolute reactance values that are different from each other, and to some measure depend on several specific characteristics of the subject, it could be useful to make the threshold values depend on the type of subject under examination. The same problem is typical of numerous measurements in pneumolbgy, for example each spirometry is accompanied by the aforementioned values for the various indices measured (vital capacity, volume expired in a second, etc.). The threshold values can thus be obtained considering equations that take into account other parameters, such as, the anthropometrical characteristics of the subjects. For this purpose it is possible, starting from the analysis of the values that the various indices assume in the various subjects belonging to a wide and heterogeneous population, to identify the correlations between the parameters that characterise the subject (for example sex, age, weight, race, height, vital capacity, functional residual capacity, etc) and its optimal threshold values for the various indices. From such correlations simple equations can be obtained that predict the optimal threshold values as function of the most significant parameters, so as to improve the specificity and sensitivity of the method.

TABLE 2

| Index | Total interval (cmH2O/l * s$^{-1}$) | Excellent interval (cmH2O/l * s$^{-1}$) | Excellent region (%) | Excellent threshold (cmH2O/l * s$^{-1}$) |
|---|---|---|---|---|
| Xrsem | −10.5 ÷ −0.3 | −4.7 ÷ −4.2 | 5.9 | −4.5 |
| Xrsm | −20.4 ÷ −0.6 | −7.6 ÷ −6.3 | 6.5 | −6.9 |
| Xrsdm | −0.6 ÷ 9.0 | 1.9 ÷ 3.4 | 15.4 | 2.7 |
| Xrspp | 0.2 ÷ 19.7 | 5.7 ÷ 6.3 | 3.1 | 6.0 |

Figure 4A:
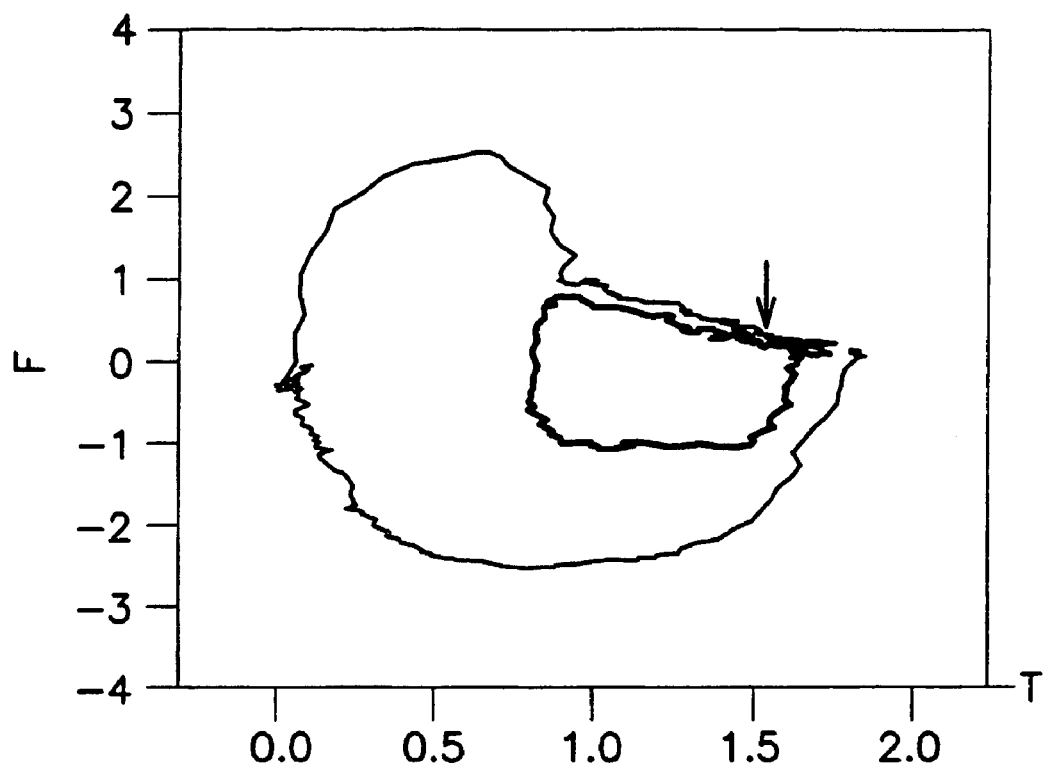
FIG. 4a shows a graph where a maximum flow-volume curve overlays a flow-volume curve obtained from spontaneous breathing.
Figure 4B:
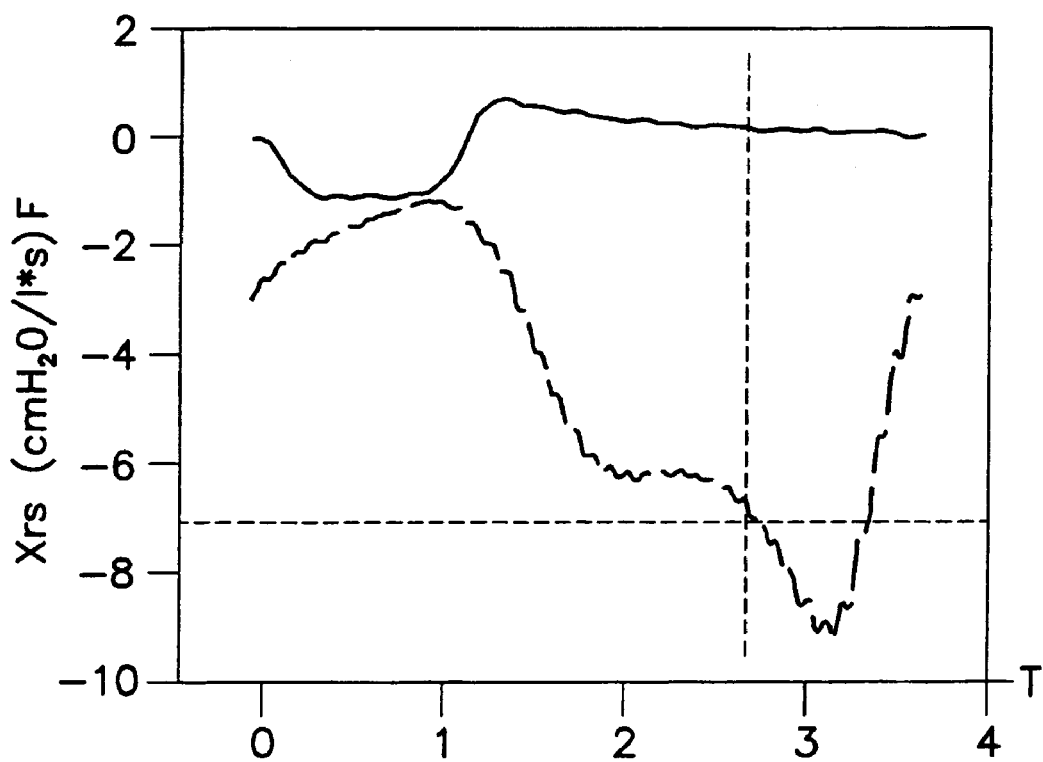
FIG. 4b shows the progress of Xrs and of the flow F over the time.

It is important to point out that while the indices calculated using the averages can discriminate if a breath is flow-limited or not, the use of the threshold values calculated for Xrsm or Xrspp can also enable the determination of the exact time in which the flow-limitation starts to occur, by carrying out the comparison with the instantaneous value of Xrs. In this case the flow-limitation conditions present can be identified only in part of the expiration (partial flow-limitation) as shown in FIG. 4a, where a maximum flow-volume curve overlays a flow-volume curve obtained from spontaneous breathing (left). The arrow points out the moment in which the two curves overlay each other, and thus when the flow-limitation phase starts. Analysing the course in time of Xrs and of the flow F (FIG. 4b) it can be seen that, when the respiration becomes flow-limited, Xrs descends below the threshold value calculated for the index Xrsm. This approach can also be applied to the study of the flow-volume curves obtained during the execution of forced partial or maximal vital capacity manoeuvres.

In addition, even though it is necessary to use only one frequency for determining whether a subject is flow-limited or not, the study of the dependence of the values of the various indices with the frequency might give useful information on localization and heterogeneity of the choke points.

The invention claimed is:

1. System for the automatic detection of expiratory flow limitation of a human subject comprising: means for determining the respiratory impedance of said human subject including a real component and an imaginary component using an expiratory phase of breathing; means for determining at least one index linked to said respiratory impedance; means for indicating the positioning of said at least one index in relation to a preset threshold value in order to detect the expiratory flow limitation.

2. System for the automatic detection of the expiratory flow limitation of a human subject in accordance with claim 1 characterised in that said means for determining at least one index is linked to the imaginary component of said respiratory impedance.

3. System for the automatic detection of the expiratory flow limitation of a human subject in accordance with claim 2 characterised in that said at least one index corresponds to the minimum value of said imaginary component reached during the expiration.

4. System for the automatic detection of the expiratory flow limitation of a human subject in accordance with claim 2 characterised in that said at least one index corresponds to the average value of said imaginary component during all or part of the expiratory phase.

5. System for the automatic detection of the expiratory flow limitation of a human subject in accordance with claim 2 characterised in that said at least one index corresponds to the difference between the maximum value of said imaginary component reached during the inspiratory phase and the minimum value of said imaginary component reached during the expiration.

6. System for the automatic detection of the expiratory flow limitation of a human subject in accordance with claim 2 characterised in that said at least one index corresponds to the difference between the average value of said imaginary component during all or part of the inspiratory phase and the average value of said imaginary component during all or part of the expiratory phase.

7. System for the automatic detection of the expiratory flow limitation of a human subject in accordance with claim 1 characterised in that said means for determining the respiratory impedance of said subject comprises: a device for generating at least one oscillating pressure signal at a preset frequency; a duct for applying said at least one oscillating pressure signal to the respiratory system of said subject; a device for measuring the flow and the pressure inside said duct.

8. System for the automatic detection of the expiratory flow limitation of a human subject in accordance with claim 7 characterised in that said means for determining the respiratory impedance of said subject comprise means for associating to each oscillating pressure signal a linear combination of sinusoids of frequencies equal to the stimulus frequencies; means for determining the impedance by means of a system at the least square; means for calculating the impedance at the various stimulus frequencies as ratio of the phasors.

9. System for the automatic detection of the expiratory flow limitation of a human subject in accordance with claim 1 characterised in that said at least one index corresponds to indices computed on the time courses of a performance index of the fitting of the impedance to a prefixed model or of the direct fitting to the flow and pressure measured at the airway opening with the prefixed model.

10. System for the automatic detection of the expiratory flow limitation of a human subject in accordance with claim 1 characterised in that the determining means determines the respiratory impedance during the spontaneous breathing of said human subject.

11. Method for the automatic detection of the expiratory flow limitation of a human subject comprising the phases of: determining the respiratory impedance of said human subject including a real component and an imaginary component using an expiratory phase of breathing; determining at least one index linked to said respiratory impedance; indicating the positioning of said at least one index in relation to a preset threshold value in order to detect the expiratory flow limitation.

12. Method for the automatic detection of the expiratory flow limitation of a human subject in accordance with claim 11 characterised in that said step of determining at least one index is linked to the imaginary component of said respiratory impedance.

13. Method for the automatic detection of the expiratory flow limitation of a human subject in accordance with claim 11 characterised in that said step of determining the respiratory impedance of said subject comprises the phases of generating at least one oscillating pressure signal at a preset frequency; applying said at least one oscillating pressure signal to the respiratory system of said subject; measuring the flow and the pressure inside a duct for applying said at least one oscillating pressure signal to the respiratory system of said human subject.

14. Method for the automatic detection of the expiratory flow limitation of a human subject in accordance with claim 11 characterised in that said at least one index is obtained assessing the difference between the inspiratory and expiratory values of said respiratory impedance of said human subject.

15. Method for the automatic detection of the expiratory flow limitation of a human subject in accordance with claim 11 characterised in that said preset threshold value is calculated on the basis of an analysis of a population of said subjects.

16. Method for the automatic detection of the expiratory flow limitation of a human subject in accordance with claim 11 characterised in that said preset threshold value is calculated on the basis of an equation that takes into account the parameters that characterise a plurality of populations of said subjects.

* * * * *